(12) United States Patent
Kimmel et al.

(10) Patent No.: US 11,934,884 B2
(45) Date of Patent: *Mar. 19, 2024

(54) COORDINATED APPLICATION PROCESSING

(71) Applicant: ILLUMINA, INC., San Diego, CA (US)

(72) Inventors: David Kimmel, San Diego, CA (US); Eunho Noh, San Diego, CA (US); Paul Smith, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/161,249

(22) Filed: Jan. 30, 2023

(65) Prior Publication Data
US 2023/0176922 A1    Jun. 8, 2023

Related U.S. Application Data

(63) Continuation of application No. 16/607,424, filed as application No. PCT/US2018/037455 on Jun. 14, 2018, now Pat. No. 11,599,394.
(Continued)

(51) Int. Cl.
*G06F 9/46* (2006.01)
*G06F 9/50* (2006.01)
(Continued)

(52) U.S. Cl.
CPC .......... *G06F 9/5066* (2013.01); *G06F 9/5033* (2013.01); *G06T 1/0007* (2013.01); *G16B 50/30* (2019.02); *G06F 2209/5017* (2013.01)

(58) Field of Classification Search
CPC ...... G06F 9/5016; G06F 9/467; G06F 9/5066; G06F 9/5033; G06N 3/04; G16B 50/30
See application file for complete search history.

(56) References Cited

U.S. PATENT DOCUMENTS 6,782,408 B1    8/2004  Chandra et al.
2003/0026505 A1    2/2003  Florent et al.
(Continued)

FOREIGN PATENT DOCUMENTS

WO    2008129536 A2    10/2008

OTHER PUBLICATIONS

Examination Report in European Application No. 18739983.7 dated Aug. 12, 2021, 9 pgs.
(Continued)

*Primary Examiner* — Tammy E Lee
(74) *Attorney, Agent, or Firm* — Matthew M. Hulihan; Heslin Rothenberg Farley & Mesiti PC

(57) ABSTRACT

Coordinated application processing includes obtaining a plurality of images and distributing them to processing engines to perform image processing. The plurality of images cover an image area, with different sub-areas, in which a biological sample to be sequenced is present. The image processing proceeds across multiple cycles to process a respective set of images, of the plurality of images, of each sub-area of the different sub-areas, and therefore of the respective area, of the flow cell, to which that sub-area correlates. The distributing the plurality of images includes, for each sub-area of the different sub-areas, distributing, across the multiple cycles of the image processing, the images of the respective set of images of that sub-area to a respective processing engine, of a plurality of processing engines, associated with, and selected for, processing images of that sub-area.

20 Claims, 9 Drawing Sheets

Related U.S. Application Data

(60) Provisional application No. 62/532,657, filed on Jul. 14, 2017.

(51) Int. Cl.
*G06T 1/00* (2006.01)
*G16B 50/30* (2019.01)

(56) References Cited

U.S. PATENT DOCUMENTS

| | | | |
|---|---|---|---|
| 2006/0012822 A1* | 1/2006 | Matsumoto | G06T 15/08 358/1.15 |
| 2006/0080389 A1 | 4/2006 | Powers et al. | |
| 2007/0192408 A1 | 8/2007 | Konig | |
| 2007/0300239 A1 | 12/2007 | Adam et al. | |
| 2008/0182757 A1 | 7/2008 | Heiner et al. | |
| 2008/0250121 A1 | 10/2008 | Thirumalai | |
| 2009/0049443 A1 | 2/2009 | Powers et al. | |
| 2009/0202149 A1* | 8/2009 | Doi | G06T 7/11 382/173 |
| 2011/0007981 A1* | 1/2011 | Osher | G01N 15/14 382/255 |
| 2012/0040657 A1 | 2/2012 | Krco et al. | |
| 2014/0267669 A1 | 9/2014 | Stoops et al. | |
| 2016/0381126 A1 | 12/2016 | Basavaiah et al. | |
| 2017/0302978 A1 | 10/2017 | Hu et al. | |
| 2018/0357107 A1* | 12/2018 | Devireddy | G06F 9/4881 |
| 2020/0133736 A1 | 4/2020 | Kimmel et al. | |

OTHER PUBLICATIONS

International Search Report and Written Opinion of the International Searching Authority for International Application No. PCT/US2018/037455 dated Sep. 5, 2018, 13 pgs.

Project Cacheonix | Distributed Java Cache, "How to Distribute Java Application on Multiple JVMs", pp. 1-3, dated Mar. 24, 2017, http://www.cacheonix.org/articles/How_to_Distribute_Java_Application_on_Multiple_JVMs.htm.

Katchabaw, M.J., et al., "Making Distributed Applications Manageable Through Instrumentation", pp. 1-26.

Office Action issued in U.S. Appl. No. 16/607,424 dated Feb. 1, 2022, 24 pgs.

Final Office Action issued in U.S. Appl. No. 16/607,424 dated Jul. 13, 2022, 15 pgs.

Advisory Action issued in U.S. Appl. No. 16/607,424 dated Oct. 6, 2022, 5 pgs.

Notice of Allowance issued in U.S. Appl. No. 16/607,424 dated Nov. 11, 2022, 10 pgs.

* cited by examiner

COORDINATED APPLICATION PROCESSING

BACKGROUND

Genomic sequencing can be a complex task that demands significant compute power. While it may be possible to distribute work to multiple nodes, it can be difficult to coordinate their execution, including the starting and stopping of sequencing package software execution, collection of runtime metrics, and distribution of work to the different nodes.

SUMMARY

Shortcomings of the prior art are overcome and additional advantages are provided through the provision of a computer-implemented method. The method includes obtaining a plurality of images, and distributing the plurality of images to a plurality of processing engines for coordinated application processing, the plurality of processing engines to perform image processing, where the plurality of images cover an image area in which the biological sample to be sequenced is present, the image area comprising multiple different sub-areas that each correlate to a respective area of a flow cell, where the plurality of images comprise images of a sequence of bases, of the biological sample, to be sequenced, where the image processing proceeds across multiple cycles of image processing to process a respective set of images, of the plurality of images, of each sub-area of the different sub-areas, and therefore of the respective area, of the flow cell, to which that sub-area correlates, and where the distributing the plurality of images comprises, for each sub-area of the different sub-areas distributing, across the multiple cycles of the image processing, the images of the respective set of images of that sub-area to a respective processing engine, of a plurality of processing engines, associated with, and selected for, processing images of that sub-area.

Further, a computer system is provided that includes memory and at least one processor, the computer system being configured to execute program instructions to perform a method. The method includes obtaining a plurality of images, and distributing the plurality of images to a plurality of processing engines for coordinated application processing, the plurality of processing engines to perform image processing, where the plurality of images cover an image area in which the biological sample to be sequenced is present, the image area comprising multiple different sub-areas that each correlate to a respective area of a flow cell, where the plurality of images comprise images of a sequence of bases, of the biological sample, to be sequenced, where the image processing proceeds across multiple cycles of image processing to process a respective set of images, of the plurality of images, of each sub-area of the different sub-areas, and therefore of the respective area, of the flow cell, to which that sub-area correlates, and where the distributing the plurality of images comprises, for each sub-area of the different sub-areas distributing, across the multiple cycles of the image processing, the images of the respective set of images of that sub-area to a respective processing engine, of a plurality of processing engines, associated with, and selected for, processing images of that sub-area.

Further, a computer program product is provided that includes a tangible storage medium storing program instructions for execution to perform a method. The method includes obtaining a plurality of images, and distributing the plurality of images to a plurality of processing engines for coordinated application processing, the plurality of processing engines to perform image processing, where the plurality of images cover an image area in which the biological sample to be sequenced is present, the image area comprising multiple different sub-areas that each correlate to a respective area of a flow cell, where the plurality of images comprise images of a sequence of bases, of the biological sample, to be sequenced, where the image processing proceeds across multiple cycles of image processing to process a respective set of images, of the plurality of images, of each sub-area of the different sub-areas, and therefore of the respective area, of the flow cell, to which that sub-area correlates, and where the distributing the plurality of images comprises, for each sub-area of the different sub-areas distributing, across the multiple cycles of the image processing, the images of the respective set of images of that sub-area to a respective processing engine, of a plurality of processing engines, associated with, and selected for, processing images of that sub-area.

In some embodiments, each processing engine of the plurality of processing engines comprises a same application package for instantiation to perform, on images received by the respective processing engine, a same set of tasks as other processing engines of the plurality of processing engines perform on images received by the other processing engines.

In some embodiments, a method further includes maintaining an image acquisition component to obtain the plurality of images and provide the plurality of images for distribution, wherein the image acquisition component is part of an application collector to perform in an image acquisition and distribution mode different from a mode under which a respective application collector on each of the plurality of processing engines is to perform.

In some embodiments, the image acquisition component acquires the plurality of images from an imaging device and wherein the method further comprises receiving, from the plurality of processing engines during performance of the image processing, scanning position information indicating guidance for an image scanning engine of the imaging device in acquiring at least some images of the plurality of images.

In some embodiments, each sub-area of the different sub-areas of the image area corresponds to a different set of one or more camera frame positions.

In some embodiments, the plurality of images are acquired during a real-time sequence analysis run to perform sequencing of the sequence of bases, and wherein the distributing the plurality of images distributes the plurality of images in real-time during the real-time sequence analysis run.

In some embodiments, a method further includes gathering, from each processing engine of the plurality of processing engines, one or more application completion communications indicating that a respective one or more portions of the image processing assigned to that processing engine are complete.

In some embodiments, a method further includes maintaining an image processing status of each processing engine of the plurality of processing engines using, at least in part, received or to-be-received application completion communications; and conveying indications of image processing status of each processing engine to a control component requesting such indications.

In some embodiments, each processing engine of the plurality of processing engines is a different physical host computer system or different virtual machine.

In some embodiments, a first processing engine of the plurality of processing engine is associated with, and selected for, processing a first set of images of a first sub-area of the different sub-areas and wherein a second processing engine of the plurality of processing engine is associated with, and selected for, processing a second set of images of a second sub-area of the different sub-areas.

In some embodiments, a same processing engine of the plurality of processing engines is associated with, and selected for, processing multiples sets of images of at least two sub-areas of the different sub-areas.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the disclosure are apparent from the following detailed description taken in conjunction with the accompanying drawings in which:

DETAILED DESCRIPTION

Described herein are facilities for distributed, coordinated application processing, for instance processing of image data by multiple instances of an analysis and sequencing software application, to perform sequencing of genomic material. An example analysis and sequencing software application is Real-Time Analysis (RTA), offered by Illumina, Inc., San Diego, California, U.S.A. Examples described herein are presented in the context, and with reference to, the RTA software, which is only by way of example; aspects described herein are equally applicable to other analysis and sequencing software applications, and more broadly any distributed, coordinated application processing.

RTA performs primary analysis in next-generation sequencing (NGS) in conjunction with the Genome Analyzer (GA) offering by Illumina, Inc. Primary analysis refers in this context to analysis up to, and including, base calling and quality scoring. RTA is multi-threaded and can work with a configurable number of threads. It is capable of executing in the background during a live sequencing run for RTA. Additionally or alternatively, it can be run using a pre-existing set of image data for off-line analysis. In one approach to leverage multithreading capability, RTA can provide each thread its own subset of tiles for which that respective thread is responsible to process, in order to help minimize thread contention.

Figure 1:
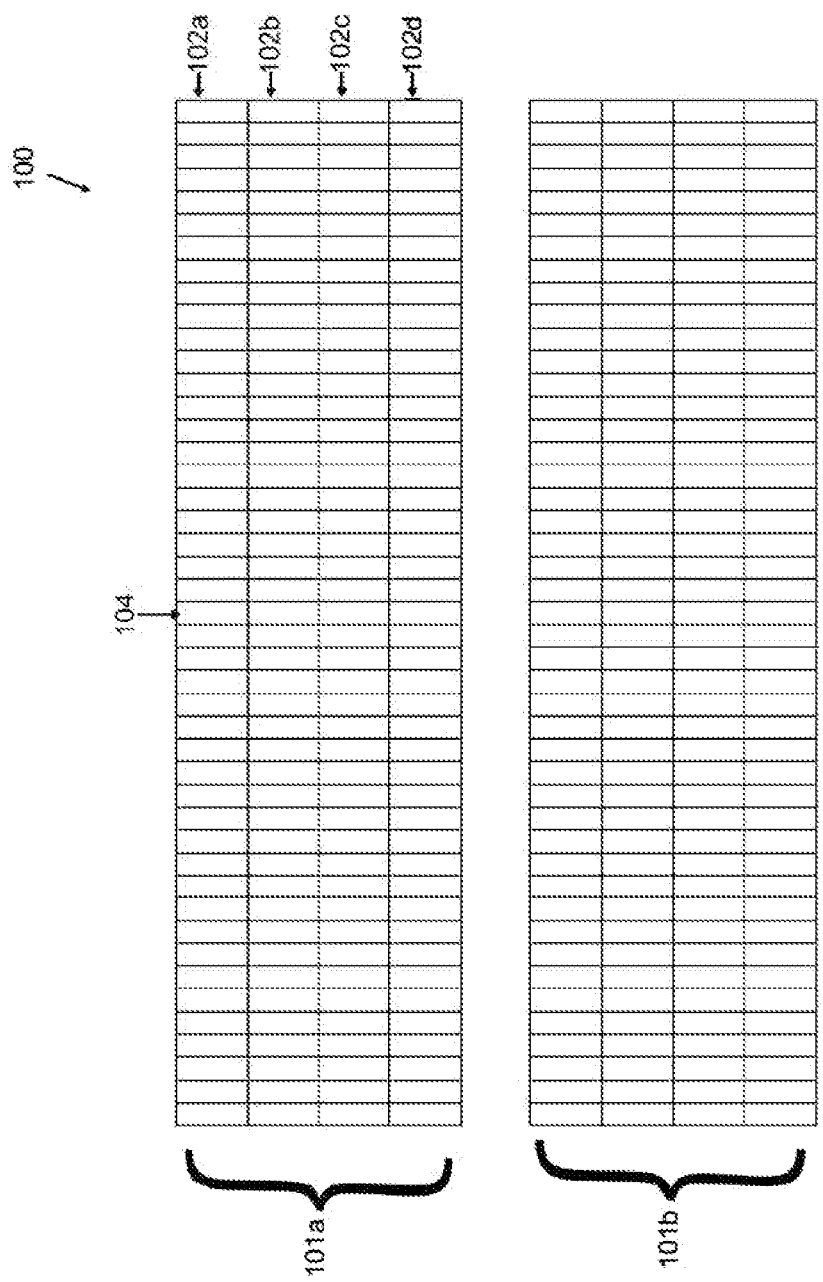
FIG. 1 depicts an example layout of a flow cell used in genomic sequencing.

RTA processing to generate sequence data proceeds in cycles against a flow cell by collecting many images of a biological sample using a sequencing device. FIG. 1 depicts an example layout of a flow cell used in genomic sequencing. Flow cell 100 includes a single surface having two lanes 101a, 101b. Each lane 101a, 101b is divided into multiple swaths and each swath is divided into tiles. Lane 101a in FIG. 1 includes swaths 102a, 102b, 102c, and 102d, each including 25 tiles (104 is a single tile). Thus, each lane in this example includes 45*4=180 tiles. Flow cell 100 includes a single surface having two lanes 101a, 101b in this example, though in other examples a flow cell includes multiple surfaces (for instance a top surface and a bottom surface) that each includes multiple lanes.

A camera interface board or other imaging device images the biological sample to generate multiple images, which are sent to RTA. This imaging covers an image area that includes many different sub-areas. A single image sent to RTA can cover a single tile of the flow cell, though it is understood that an image may cover an area larger or smaller than a single tile. For instance, an image may actually cover multiple tiles, a single swath, etc.

RTA processing proceeds in cycles during which the sample is re-imaged at each cycle. Thus, a given tile may be imaged during each cycle and, as a result, the imaging across the cycles produces a respective set of images (of the entire set of images) of each sub-area-tile in this example.

Images are passed in memory to the RTA application as tiles of the flow cell, where each tile may be one field-of-view of the camera or some/all of a single swath (as examples) on a line scanning system. The basecall(s) generated from an image may be written out to a binary file (e.g. *.bcl) per cycle.

The primary inputs to RTA are these images contained in local system memory. The images are created by the scanning system and can be transferred to RTA via an inter-process communication mechanism and/or loaded by RTA from a user-specified path in off-line mode. The primary output files that RTA produces are .bcl and filter files.

RTA in some examples runs locally on the instrument computer system, a computer system associated with, and usually physically located with, the instrument, in order to control its operation. The image processing functions of RTA include, as examples, extracting intensities from the acquired images, performing basecalling, quality scoring the bases, aligning to the Phi X reference genome, and reporting data in binary InterOp files for viewing in the Sequencing Analysis Viewer application offered by Illumina, Inc.

It may be desired to distribute the RTA processing across multiple nodes, each executing an instance of RTA, in order to take advantage of the enhancement offered by distributed processing. However, as noted above, it can be difficult to coordinate the execution of the application instances, including the starting and stopping of RTA execution, collection of runtime metrics, and distribution of work to the appropriate nodes. RTA processes the tiles for each of several cycles and expects to receive, for a given tile, the image(s) of that tile at each of the cycles. There are multiple images delivered for each sub-area of the image area being imaged at each cycle.

In order to properly process the image data of a given sub-area at a given cycle, cycle data (i.e. data from an image of that sub-area from a different cycle) from previous/next cycle(s) may be needed or desired in order for the RTA instance processing that data at the given cycle to properly and efficiently process the current cycle data. Accounting for the foregoing is not as much a concern when the RTA processing is by a single RTA instance on a single computer. When the RTA processing is distributed to multiple RTA instances, the inter-dependency between cycles is to be addressed.

This problem of controlling multiple instances of RTA across multiple compute nodes to conduct primary analysis is addressed by aspects described herein, specifically by running (executing) an application distributor ("app distributor") on a distribution engine (DE), the app distributor to distribute the application, and an application collector ("app collector") on each of a plurality of processing engines (PE) to run the distributed application. The app distributor coordinates the distribution of images acquired for image processing to the distributed application instances. This coordinated distribution can include identification of which processing engine is to receive given image data. An image of a first area (a first sub-area of a larger image area) is received and distributed to a first processing engine, an image of a second area (a second sub-area of the larger image area) is received and distributed to a second processing engine, and so on. When a next image of the first area is received (e.g. at a next cycle), the above-described dependency aspect is addressed by actively selecting the first processing engine as the one to which the next image of the first area is provided.

Accordingly, there are multiple images to cover an image area, such as a flow cell, for a given cycle. These images can be distributed out to the processing engines depending on how many processing engines are available. When processing proceeds to a next cycle in sequencing, another multiple images that cover the image area may be acquired. There is correlation between an image from this subsequent cycle and an image from the prior cycle, the correlation being that the images are of a common, possibly overlapping area or position in the flow cell called a sub-area. This may be the case for many images of the multiple images that cover the flow cell in this subsequent cycle—each correlates to a prior-acquired image from the prior cycle. These images may be distributed to the processing engines in a manner that distributes correlated images to the same processing engine. In a particular example, each image covers a respective swath (the sub-area in this example) of a flow cell (the image area in this example) and therefore a common processing engine may process the set of images, taken across the multiple cycles, that cover that swath.

An application manage package includes two applications:

App Distributor—The app distributor identifies, via multicasting or any other appropriate approach, the addresses and ports of available app collectors on the network, and distributes the target application, e.g. RTA, to available app collectors on individual processing engines. In a particular example, the app distributor distributes the app using Boost serialized messages embedded in HTTP (Boost refers to a set of libraries offered at www dot boost dot org), though app distribution may be accomplished through any other appropriate means.

App Collector—The app collector receives the target application from the app distributor and launches it using settings provided by the distributor.

Figure 2:
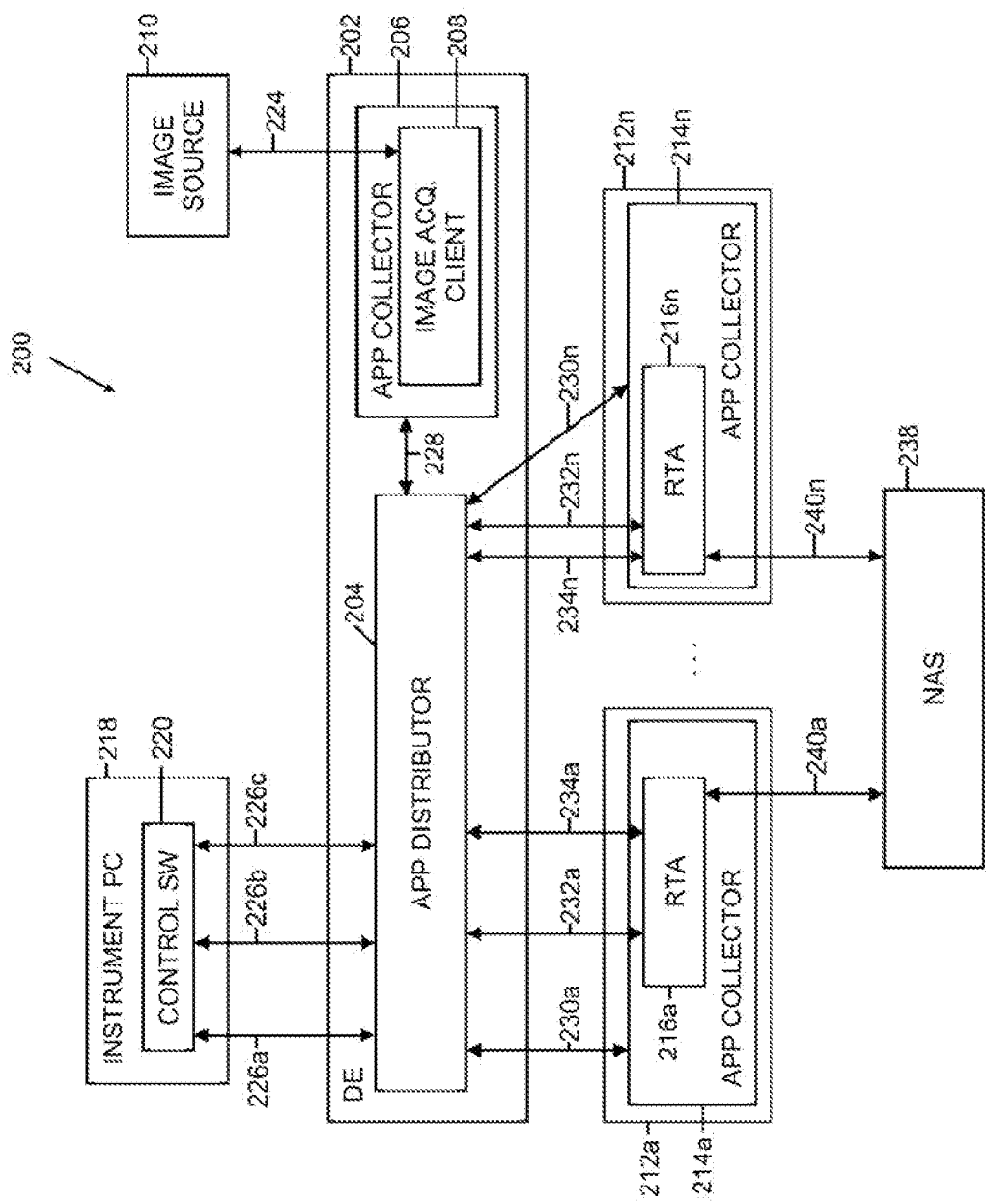
FIG. 2 depicts an example computing environment to incorporate and use aspects described herein.

Further details and explanation are provided with reference to FIG. 2, which depicts an example computing environment 200 to incorporate and use aspects described herein. Distribution engine (DE) 202 includes an application distributor 204 and application collector 206. Distribution engine 202 may be implemented as one or more computer system(s) and/or virtual machine(s), as examples.

Application collector 206 includes an image acquisition client 208 application that interfaces with an image source 210 to collect the images. The image source 210 may be a simulator or repository of images, and/or a component of the sequencer (not pictured), for instance an imaging device/camera interface board that captures images.

The image source 210 provides the images to the image acquisition client 208 and/or the image acquisition client 208 retrieves the images from the image source 210 via a communication link 224 extending between the two components. Communications links include wired and/or wireless communications links, such as Ethernet-based wired and/or Wi-Fi connections, cellular connections, or the like. More broadly, communications links may be any appropriate wireless or wired communication links for communicating data. In a particular example, the image source and image acquisition client communicate via a base address register space, which may be a portion of memory designated for communication of messages or other data between the camera interface board and the component collecting the images.

One function of the distribution engine 202 is to distribute the acquired images to multiple processing engines (PEs) 212a, . . . , 212n, to conduct primary analysis, and do so such that, for any given sub-area of the overall image area being imaged, the same application instance processes the images of that sub-area across all cycles.

The image acquisition client 208 can provide the images to the application distributor 204 for distribution to the processing engines. Alternatively, the image acquisition client 208 may provide the images directly to the processing engines instead of doing so via the application distributor 204. One way for the distribution engine or component thereof to track which instance is to process an arriving image for a given tile (or other sub-area) is to associate a unique identifier with each tile/sub-area and correlate that to a given processing engine or application instance. When an image arrives, the identifier is ascertained to identify which sub-area the arriving image covers, and provide the image to the appropriate application instance for processing.

Processing engines are nodes implemented by computer systems, virtual machines, and/or any other desired entity that can process data. Each processing engine (212a, . . . , 212n) runs a respective application collector (214a, . . . , 214n), and each such app collector runs a respective instance (216a, . . . , 216n) of the RTA application that is instantiated from an image that the processing engine receives from the distribution engine. In some examples, it is desired to ensure that the same version of the processing software (e.g. RTA) is used across the nodes and that the applications are coordinated in terms of their launch and execution. Thus, as explained in further detail below, the application distributor 204 can distribute an image of the application to each of the processing nodes for instantiation with each new sequencing run, to help ensure that the same revision of the application is executed at each processing node. Distributing the application to the processing engines can include distributing the same application package to each processing engine, the application package being for instantiation on each processing engine as an instance of the application, which is configured to perform the same set of tasks as the application instances on the other processing engines. The application distributor 204 can communicate with the application collectors via HTTP messaging or any other communication approach.

Also shown in FIG. 1 is an instrument PC 218, which is the computer system associated with the instrument (e.g. sequencer). The instrument may be included as part of or in physical proximity to the instrument. Instrument PC 218 includes control software 220 to control operation of the instrument, for instance to control starting and stopping of a sequencing run, and issue controls to other components. The control software 220 and distribution engine 202, specifically the application distributor 204 thereof, communicate with each other over communication link(s) 226a, 226b, 226c. Separate communication links are shown in FIG. 1 to illustrate logical separation, however these links may be implemented as one or more physical links between the components. The distribution engine 202 includes an interface through which an administrator and/or software can invoke commands via these links. In a particular example, sequencing start and stop requests/replies are communicated via link 226a, sequencing status requests/replies are communicated via link 226b, and registration offsets requests/replies are communicated via link 226c.

Application distributor 204 communicates with application collector 206 across communication link 228, for instance to pass sequencing start and stop requests/replies. For example, the application distributor communicates with the application collector to inform that the application collector is to commence image acquisition and provision based on the commencement of a sequencing run.

The application distributor 204 also acquires from the application collector 206 the images that the application collector acquires, and distributes those images to the RTA instances 216a, . . . , 216n for processing. The application distributor 204 communicates via links 230a, . . . , 230n with the application collectors 214a, . . . , 214n installed on the processing nodes to exchange sequencing start and stop requests/replies.

The application distributor 204 communicates via links 232a, . . . , 232n with the RTA instances 216a, . . . , 216n to exchange sequencing status requests/replies, and via links 234a, . . . , 234n to exchange registration offset requests/replies.

The application instances 216a, . . . , 216n can perform in any desired manner, for instance the manner in which they might perform if not in a coordinated processing environment. By way of specific example, the RTA instances can perform RTA processing as is currently performed. As part of this, the RTA instances may write data out to any desired location, for instance a hard drive or other local storage device, or network storage 238 across communication links 240a, . . . , 240n, as examples. The output of the RTAs may at some point be aggregated by a component that reads the output from NAS 238 or extracts the output from each of the nodes. Alternatively, an RTA instance, application collector, or processing engine may be responsible for providing the output to another process, component, remote computer system, or the like. Example output from the RTA instances include data in the *.bcl format (a binary file relating to base calls of the sequence) and other data currently associated with RTA processing, for instance metrics from the sequencing run and filter files, as examples.

In some examples, the processing engines provide information via HTTP or other messaging back to the distribution engine, for example metrics that the distribution engine may need or desire. For instance, the distribution engine may collect information from the processing engines that helps the scanning engine. Example information includes coordinate information that informs adjustments for drift in the location of the flow cells and assists in image registration.

The application collector 206 may be identical to the application collectors 214a, . . . , 214n running on the processing engines except that it is configured to perform in an image acquisition and distribution mode to distribute the images to the processing engines or application distributor, which mode is different from a mode under which each application collector on the processing engines is configured to perform. Thus, the application collector 206 on the distribution engine 202 may not run an RTA instance but may run an image distributor application that keeps track of which acquired images are to be provided to which particular RTA instances on the processing engines. Alternatively, the application collector 206 on the distribution engine may, if desired, function like the others do by executing an instance of RTA to behave like another node for RTA processing.

The components of FIG. 1 may be implemented as one or more physical host machines (computer systems), though in some examples, one or more such components are run as/in virtual machines.

Figure 3:
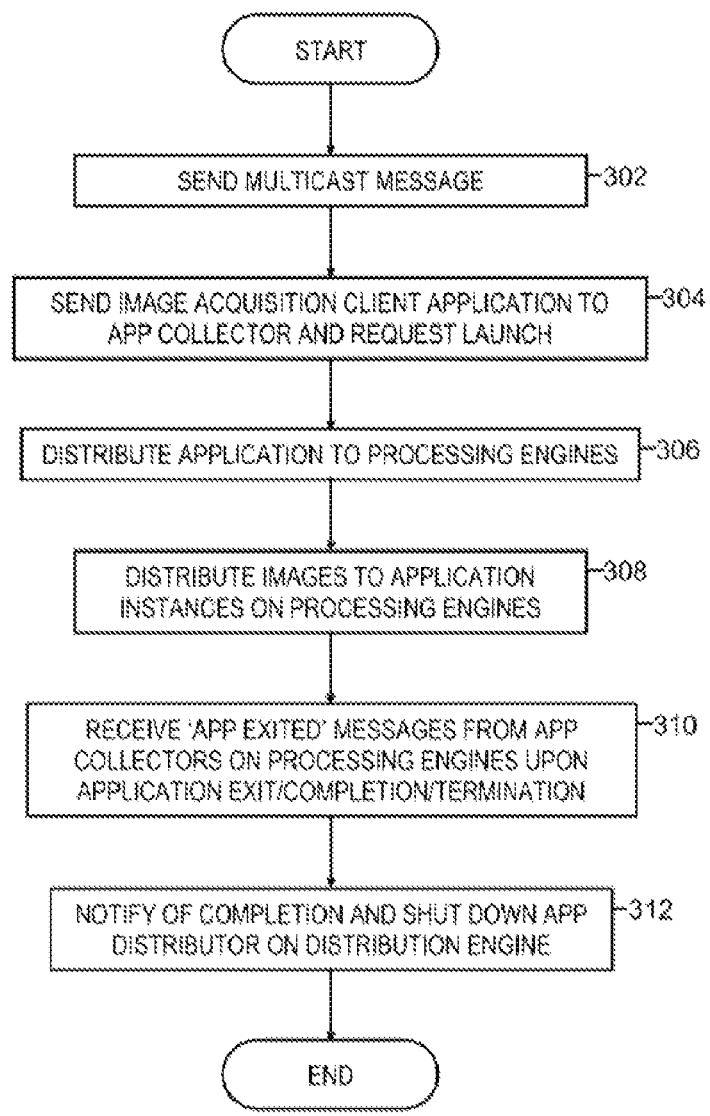
FIG. 3 depicts an example method for coordinated real-time analysis processing, in accordance with aspects described herein.

FIG. 3 depicts an example method for coordinated real-time analysis processing, in accordance with aspects described herein. Aspects of FIG. 3 are performed by computer system(s), for instance a distribution engine computer system, processing engine computer system, and/or an instrument computer system.

The process begins with the application distributor sending a multicast message (or any other desired type of message) to ascertain the addresses of available processing engines (302). The application collectors on the nodes respond, if available. Responses to the multicast message are received by the application distributor to identify the processing engines that are available in the computing environment for coordinated application processing. The sending of this multicast message is in some examples triggered by a 'sequencing start request' received by the distribution engine from the control software, informing the distribution engine of the start of a sequence run.

The process proceeds with the application distributor sending the image acquisition client application to the application collector of the distribution engine, and requesting launch thereof (304). In a particular example, the application distributor sends this through the loopback address (127.0.0.1) and requests that the distribution engine launch the image acquisition client application.

The application distributor then distributes the application to the processing engines (306), for instance the processing engines discovered based on the sending of the multicast message and responses thereto. The trigger for distribution of the application may be an application programming interface (API) trigger or other communication made from the control software to the application distributor informing of a run start. The application distributor can also explicitly request the processing engines to instantiate/launch the application distributed. In a particular example, the application distributor sends an application package in the form of an image (disk, ISO, RAM, executable, etc. image), compressed file, or the like of the application (e.g. RTA) to the processing engine application collectors for instantiation. The application can be sent through a dedicated, high-throughput connection. This high-throughput connection may also be utilized as the connection over which the images are distributed to the processing engines, because speed and reliability in moving the images to the appropriate application instance may be desirable.

The image acquisition client, application distributor, or other component of the distribution engine distributes images to the processing engines, e.g. the application instances executing thereon (308). The applications process the received images in any way desired, for instance in the manner of current RTA processing. The distribution may be performed in real-time as the images are collected from the sequencer.

The application collector of each participating processing engine sends, and the application distributor receives, an 'app exited' message upon exit/completion/termination of the application running on the particular processing engine (310). The application distributor may receive the 'app exited' messages from the processing engines over time as each individual application instance finishes processing the images provided to it and terminates. The application collector on the distribution engine may or may not send an 'app exited' message as well. The application collector on the distribution engine may be aware (e.g. by a communication from the application distributor) of when the sequencing run ends, signifying that the application collector on the distribution engine has no further images to acquire and provide to the distributor and/or RTA instances. The application collector can then exit and send a communication to the application distributor, if desired. In this manner, the application collector on the distribution engine may be regarded as another worker node that the application distributor expects to have exited before concluding the processing of the run.

The application distributor, once application collectors have provided the appropriate message, can then notify the control software that the sequencing run is finished, and then shut down (312). Alternatively, the application distributor may persist and monitor for the start of subsequent runs.

The distribution engine may be aware of the status of application processing on each processing engine. RTA, for instance, includes a server that allows users to query for information including RTA readiness, running status, and x-y offsets. This can be leveraged to support a control API or other interface allowing an administrator or other user to query the status of application(s). The querying may occur during processing, in which messages are exchanged between the distribution engine and the application collectors on the processing engines in order to deliver application status.

Figure 4:
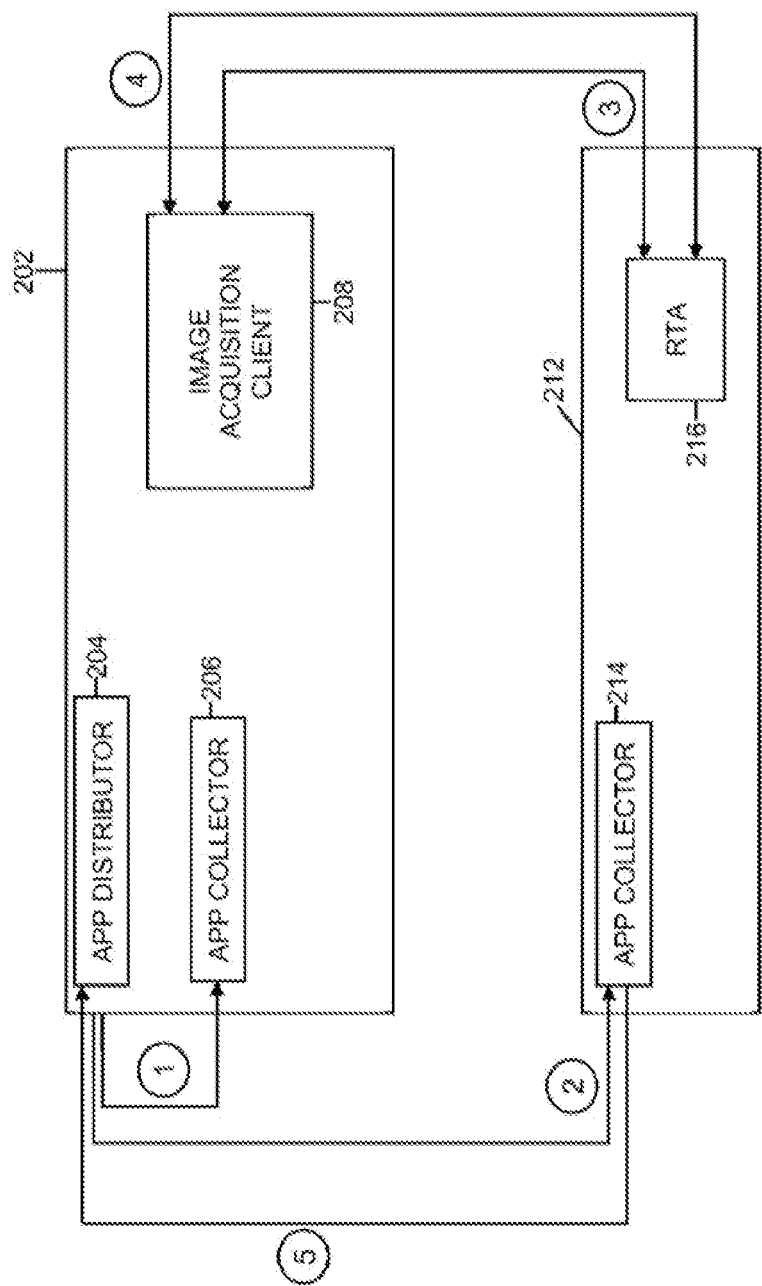
FIG. 4 depicts example communications between a distribution engine and a processing engine, in accordance with aspects described herein.

FIG. 4 depicts example communications between a distribution engine and a processing engine of FIG. 2, in accordance with aspects described herein. At 1, the application distributor 204 of distribution engine 202 sends the image acquisition client application 208 to the application collector 206 of the distribution engine 202 (corresponding to 304 of FIG. 3). This may be sent via the loopback address, as an example. At 2, the application distributor 204 sends the application package for application 216 to the application collector 214 of processing engine 212 (corresponding to 306 of FIG. 3). Communication between the application distributor 204 and application collector 214 may be made on port 9035 (or any other desired port) and include 'AppAdd' requests, Status requests, and 'AppStop' requests, as examples. At 3, the image acquisition component 208 sends images to the application 216 on port 9036 (or any other desired port). At 4, the application 216 sends a free image request to the image acquisition client 208 on a port specified for the processing engine 212 (each processing engine may have an assigned port number through which it is to send messages to the image acquisition client 208). RTA has a limited number of image buffers for storing incoming images. The application distributor can keep track of the number of free (empty/available) image buffers that each RTA instance has and send new images only when there are available buffer(s). The free image request noted above is an example approach for the RTA instance to communicate to the application distributor that an image buffer has been freed. At 5, the application collector 214 sends an 'AppExited' message to the application distributor 204 on port 9034 (or any other desired port).

Distributed, coordinated application processing in accordance with aspects described herein provides practically unlimited scalability to primary analysis. The application manager package that includes the application collector and distributor on the distribution engine gives centralized control over multiple RTA instances executing on separate processing nodes. The application manager package enables efficient control and coordination over the distributed processing by (i) automatically detecting available processing engines in the network or other computing environment; (ii) launching multiple RTA applications on different machines automatically; and (iii) providing the ability to query the status of RTA instances via the distribution engine.

In accordance with some aspects described herein, the image data is distributed down to the RTA instances for processing without a requirement that any output of the processing be gathered back by the distribution component. The desired output may be placed elsewhere and/or picked up by another downstream component for handling, for example. In addition, the routing of the images ensures consistency in which RTA instance is processing the images of a given tile or other sub-area of an area being imaged, across each of the multiple processing cycles, thereby respecting a dependency in the processing that exists between the processing cycles.

Figure 5:
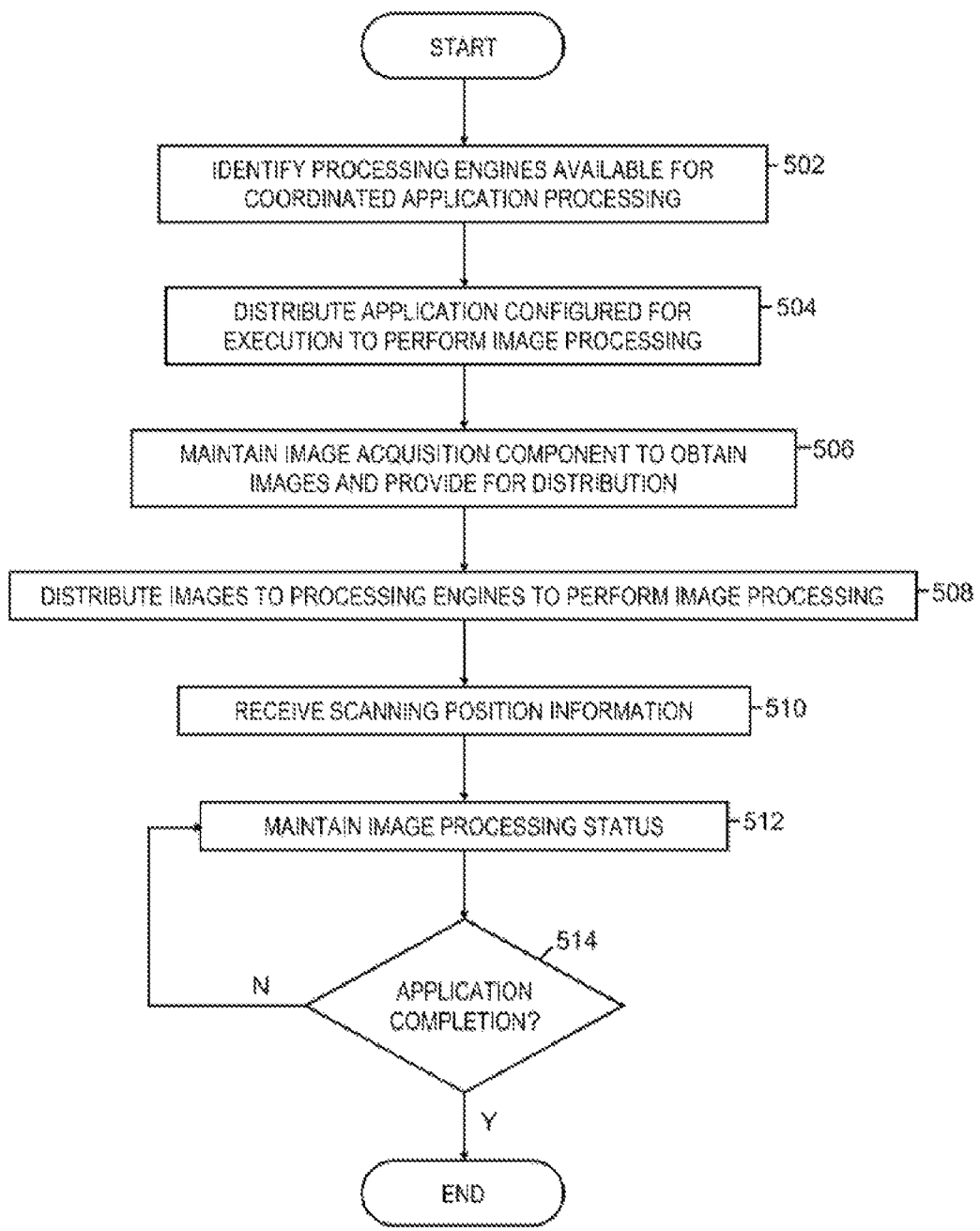
FIG. 5 depicts an example process for coordinated application processing, in accordance with aspects described herein.

Accordingly, FIG. 5 depicts an example process for coordinated application processing, in accordance with aspects described herein. In some examples, the process is performed by one or more computer systems, such as those described herein, which may include one or more computer systems running a distribution engine and/or components thereof, and/or one or more other computer systems.

The process of FIG. 5 includes identifying a plurality of processing engines available in a computing environment for coordinated application processing (502). The plurality of processing engines may be a different physical host computer system or different virtual machine. The process continues by distributing to the plurality of processing engines an application configured for execution to perform image processing (504). One such example application is Real-Time Analysis. The distributing the application to the plurality of processing engines can include distributing a same application package to each processing engine of the plurality of processing engines, the application package being for instantiation on each processing engine as an instance of the application. Each such application instance may be configured to perform identically, i.e. perform a same set of tasks (albeit against different images) as the application instances instantiated from the application package on each of the other processing engines of the plurality of processing engines.

The process of FIG. 5 also maintains an image acquisition component configured to obtain a plurality of images and provide the plurality of images for distribution (506). The image acquisition component may be part of an application collector of a distribution engine, the application collector configured to perform in an image acquisition and distribution mode that is different from a mode under which each application collector on the plurality of processing engines is configured to perform.

The process distributes the plurality of images to the plurality of processing engines to perform the image processing (508). The plurality of images can cover an image area that includes multiple different (i.e. at least partially non-overlapping) sub-areas. Each sub-area of the different sub-areas of the image area can correspond to a different set of one or more camera frame positions. The image processing proceeds across multiple cycles of image processing to process a respective set of images, of the plurality of images, of each sub-area of the different sub-areas. Thus, for each sub-area, there are one or more image(s) of that sub-area for each cycle of the multiple cycles of processing. This results in, for each sub-area, a respective set of images of that sub-area, the respective set including the images of that sub-area acquired across the cycles. Further details of the distribution of the images are provided with reference to FIG. 5. In some examples, the image acquisition component itself distributes the images down to the processing engines. Alternatively, the image acquisition component can provide the images to the application distributor on the distribution engine for distribution to the processing engines.

The plurality of images may be acquired from an imaging device. Thus, the process of FIG. 5 includes receiving, from the plurality of processing engines during performance of the image processing, scanning position information indicating guidance for an image scanning engine of the imaging device in acquiring at least some images of the plurality of images (510). The processing engines in this manner can return information back to the distribution engine to aid in camera/scanner positioning.

The process also maintains an image processing status of each processing engine of the plurality of processing engines based at least in part on received or to-be-received application completion communications (512). If an app 'exited' or 'completion' communication has not yet been received from a given processing engine, the status of the processing engine and/or application instance on that processing engine may be assumed to be active. Optionally, the process includes conveying indications of image processing status of each processing engine to a control component requesting such indications.

The process of FIG. 5 also gathers from each processing engine of the plurality of processing engines one or more application completion communications indicating that a respective one or more portions of the image processing assigned to that processing engine are complete. The completion communications can include not only app completion/termination messages regarding completion of the multiple cycles, but any status messages sent from the processing engine during processing and regarding status or completion of a particular cycle. Accordingly, the process determines whether all application completion communications have been received from all processing engines (514). If not, the process returns to (512) to continue maintaining the image process status. Otherwise, application completion was signaled and the process ends.

Figure 6:
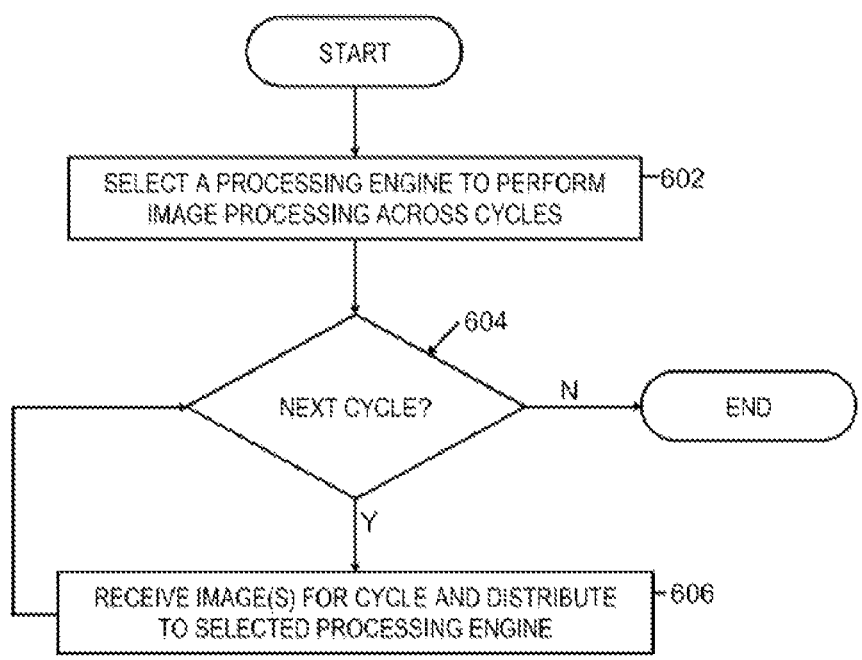
FIG. 6 depicts an example process for distributing images to a plurality of processing engines, in accordance with aspects described herein.

In a particular example, the plurality of images include images of a sequence of bases, the images of the sequence of bases acquired during a real-time sequence analysis run to perform sequencing of the sequence of bases, and the distributing the plurality of images is performed in real-time during the real-time sequence analysis run FIG. 6 depicts an example process for distributing images to a plurality of processing engines, in accordance with aspects described herein. The process of FIG. 6 is performed with respect to a given sub-area, and it may be performed for each sub-area of the different sub-areas. The process is performed by one or more computer systems, for instance one or more that execute a distribution engine or component(s) thereof. The process includes selecting, for that sub-area, a respective processing engine of the plurality of processing engines to perform the image processing across the multiple cycles to process the respective set of images of that sub-area (602). Thus, a selected (single) processing engine is to perform the processing for each of the images, of the plurality, in the set of images of the subject sub-area. The process then enters a loop until there is no next cycle for which images are to be received and distributed. The process determines whether there is a next cycle (604). If so (604, Y), the process receives the image(s) for the cycle and distributes the image(s) to the selected processing engine (606), then returns to 604. This repeats as long as there are next cycles. The distribution selects, at each iteration, e.g. at each cycle, the same processing engine to process images of the sub-area. Eventually, there is no next cycle (604, N), and the process ends. Distribution in this manner distributes, across the multiple cycles of the image processing, the images of the respective set of images of that sub-area to the respective processing engine selected for that sub-area. As the process proceeds though the cycles, the images that are in the set are of images of the given sub-area are distributed to the selected processing engine for processing.

Different processing engines can process images of different sub-areas; the selecting can select one processing engine of the plurality of processing engine to process a first set of images of a first sub-area of the different sub-areas and select a different processing engine of the plurality of processing engine to process a second set of images of a second sub-area of the different sub-areas. In some example, a common processing engine is selected to process images of more than one sub-area. Thus, the selecting can select a same processing engine of the plurality of processing engines to process set of images of at least two sub-areas of the different sub-areas.

Although various examples are provided, variations are possible without departing from a spirit of the claimed aspects.

Figure 7:
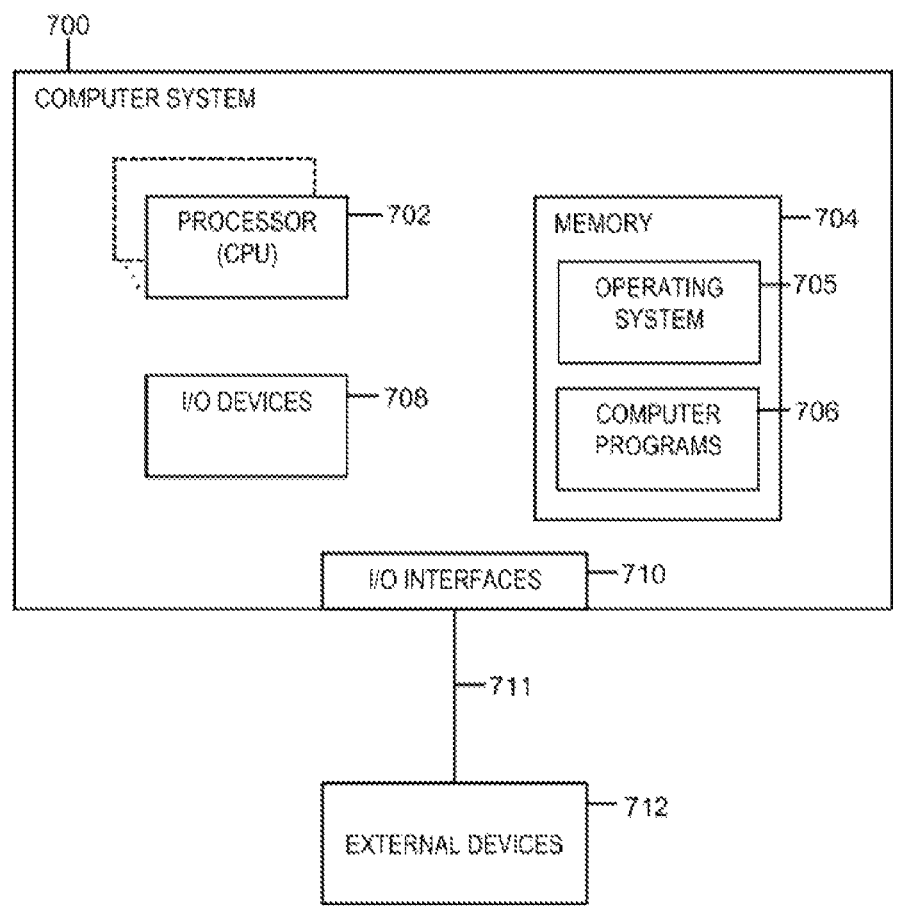
FIG. 7 depicts one example of a computer system and associated devices to incorporate and/or use aspects described herein.

Processes described herein may be performed singly or collectively by one or more computer systems. In some examples, these computer system(s) are cloud-hosted. FIG. 7 depicts one example of such a computer system and associated devices to incorporate and/or use aspects described herein. A computer system may also be referred to herein as a data processing device/system, computing device/system/node, or simply a computer. The computer system may be based on one or more of various system architectures and/or instruction set architectures, such as those offered by Intel Corporation (Santa Clara, California, USA), as an example.

FIG. 7 shows a computer system 700 in communication with external device(s) 712. Computer system 700 includes one or more processor(s) 702, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 702 can also include register(s) to be used by one or more of the functional components. Computer system 700 also includes memory 704, input/output (I/O) devices 708, and I/O interfaces 710, which may be coupled to processor(s) 702 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 704 can be or include main or system memory (e.g. Random Access Memory) used in the execution of program instructions, storage device(s) such as hard drive(s), flash media, or optical media as examples, and/or cache memory, as examples. Memory 704 can include, for instance, a cache, such as a shared cache, which may be coupled to local caches (examples include L1 cache, L2 cache, etc.) of processor(s) 702. Additionally, memory 704 may be or include at least one computer program product having a set (e.g., at least one) of program modules, instructions, code or the like that is/are configured to carry out functions of examples described herein when executed by one or more processors.

Memory 704 can store an operating system 705 and other computer programs 706, such as one or more computer programs/applications that execute to perform aspects described herein. Specifically, programs/applications can include computer readable program instructions that may be configured to carry out functions of examples of aspects described herein.

Examples of I/O devices 708 include but are not limited to microphones, speakers, Global Positioning System (GPS) devices, cameras, lights, accelerometers, gyroscopes, magnetometers, sensor devices configured to sense light, proximity, heart rate, body and/or ambient temperature, blood pressure, and/or skin resistance, and activity monitors. An I/O device may be incorporated into the computer system as shown, though in some examples an I/O device may be regarded as an external device (712) coupled to the computer system through one or more I/O interfaces 710.

Computer system 700 may communicate with one or more external devices 712 via one or more I/O interfaces 710. Example external devices include a keyboard, a pointing device, a display, and/or any other devices that enable a user to interact with computer system 700. Other example external devices include any device that enables computer system 700 to communicate with one or more other computing systems or peripheral devices such as a printer. A network interface/adapter is an example I/O interface that enables computer system 700 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems (BLUETOOTH is a registered trademark of Bluetooth SIG, Inc., Kirkland, Washington, U.S.A.).

The communication between I/O interfaces 710 and external devices 712 can occur across wired and/or wireless communications link(s) 711, such as Ethernet-based wired or wireless connections. Example wireless connections include cellular, Wi-Fi, Bluetooth®, proximity-based, near-field, or other types of wireless connections. More broadly, communications link(s) 711 may be any appropriate wireless and/or wired communication link(s) for communicating data.

Particular external device(s) 712 may include one or more data storage devices, which may store one or more programs, one or more computer readable program instructions, and/or data, etc. Computer system 700 may include and/or be coupled to and in communication with (e.g. as an external device of the computer system) removable/non-removable, volatile/non-volatile computer system storage media. For example, it may include and/or be coupled to a non-removable, non-volatile magnetic media (may be called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media.

Computer system 700 may be operational with numerous other general purpose or special purpose computing system environments or configurations. Computer system 700 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

Figure 8:
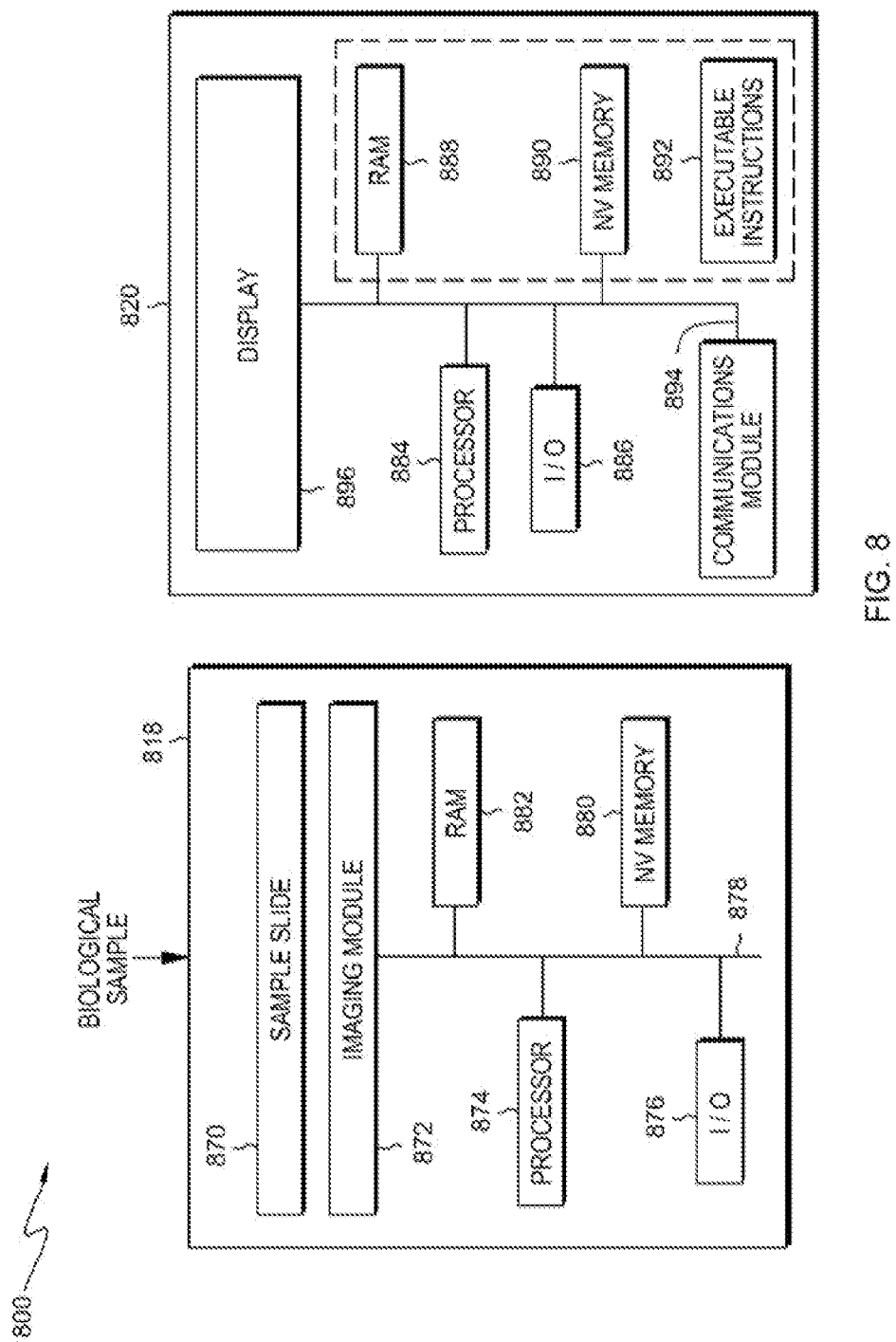
FIG. 8 depicts one example of a sequencing device that may be used in conjunction with aspects described herein.

Further aspects of sequencing using a computer system are now described. FIG. 8 is a schematic diagram of the sequencing device 800 that may be used in conjunction with, for instance, a cloud computing environment described with reference to FIG. 9. The sequencing device 800 may be implemented according to any sequencing technique, such as those incorporating sequencing-by-synthesis methods or sequencing by ligation techniques. Some examples can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore. Yet other examples include detection of a proton released upon incorporation of a nucleotide into an extension product. For example, sequencing based on detection of released protons can use an electrical detector and associated techniques. Particular examples can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides. Other suitable alternative techniques include, for example, fluorescent in situ sequencing (FIS-SEQ), and Massively Parallel Signature Sequencing (MPSS). In particular examples, the sequencing device 800 may be a HiSeq, MiSeq, or HiScanSQ from Illumina Inc.

In the depicted example, the sequencing device 800 includes a separate sample processing device 818 and an associated computer system 820. However, as noted, these may be implemented as a single device. Further, the associated computer 820 may be local to or networked with (e.g. as a cloud or other remote offering) the sample processing device 818. In some examples, the computer 820 may be a cloud computing device that is remote from the sequencing device 800. That is, the computer 820 may be capable of communicating with the sequencing device 800 through a cloud computing environment. In the depicted example, the biological sample may be loaded into the sample processing device 818 as a sample slide 870 that is imaged to generate sequence data. For example, reagents that interact with the biological sample fluoresce at particular wavelengths in response to an excitation beam generated by an imaging module 872 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through directing optics. This retrobeam may be directed toward detection optics of the imaging module 872.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning. Other useful detectors are described in the context of various nucleic acid sequencing methodologies.

The imaging module 872 may be under processor control, e.g., via a processor 874, and the sample receiving device 818 may also include I/O controls 876, an internal bus 878, non-volatile memory 880, RAM 882 and any other memory structure such that the memory is capable of storing executable instructions, and other suitable hardware components that may be similar to those described with regard to FIG. 7. Further, the associated computer 820 may also include a processor 884, I/O controls 886, a communications module 887, and a memory architecture including RAM 888 and non-volatile memory 890, such that the memory architecture is capable of storing executable instructions 892. The hardware components may be linked by an internal bus 894, which may also link to the display 896. In examples in which the sequencing device is implemented as an all-in-one device, certain redundant hardware elements may be eliminated.

Figure 9:
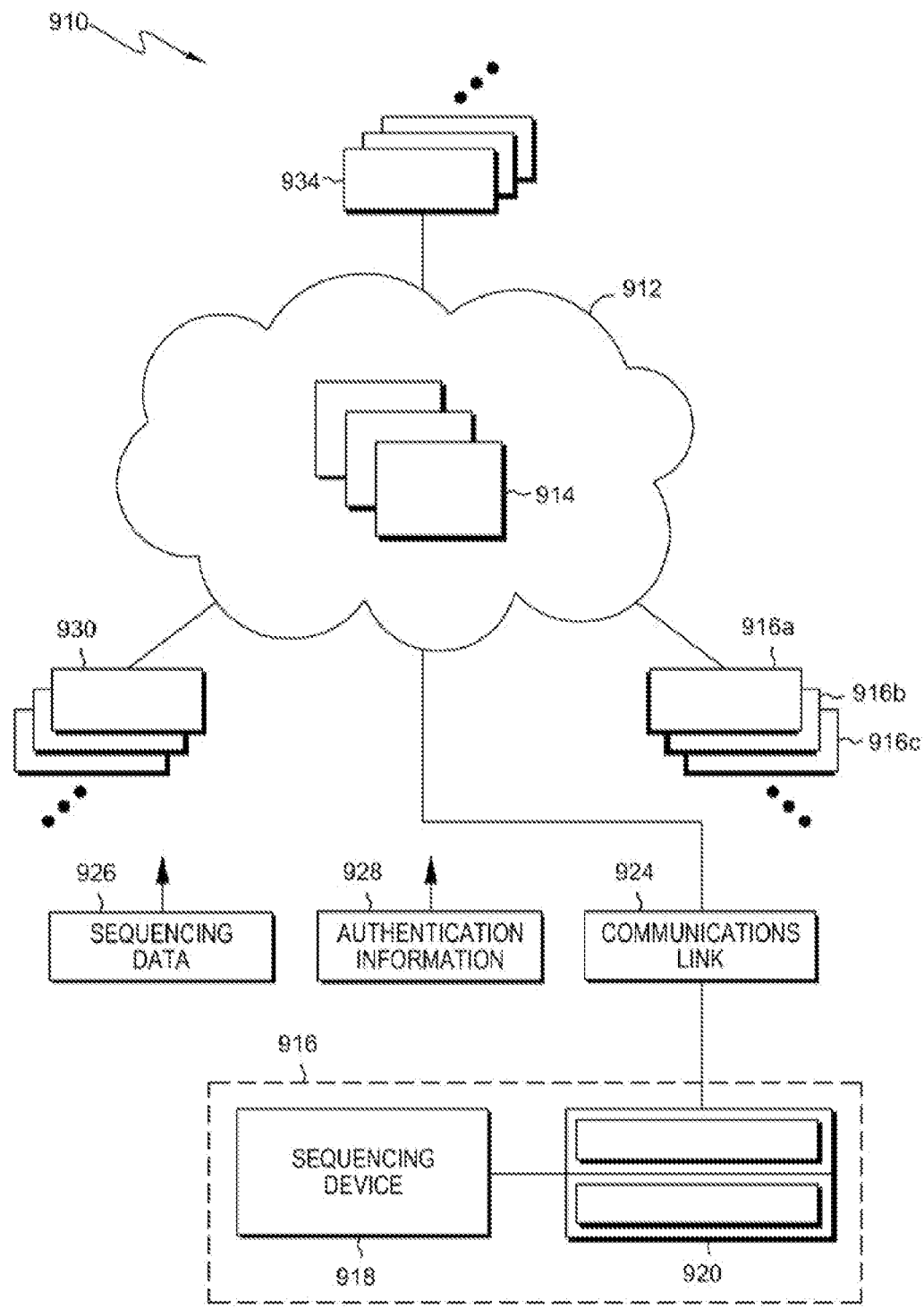
FIG. 9 depicts one example of a cloud computing environment in accordance with aspects described herein.

Turning now to FIG. 9, a cloud computing environment 910 for biological data is illustrated diagrammatically. As used herein, the term "cloud" or "cloud computing environment" may refer to various evolving arrangements, infrastructure, networks, and the like that may be based upon the Internet. The term may refer to any type of cloud, including client clouds, application clouds, platform clouds, infrastructure clouds, server clouds, and so forth. As will be appreciated by those skilled in the art, such arrangements may allow for use by owners or users of sequencing devices, provide software as a service (SaaS), provide various aspects of computing platforms as a service (PaaS), provide various network infrastructures as a service (IaaS) and so forth. Moreover, included in this term should be various types and business arrangements for these products and services, including public clouds, community clouds, hybrid clouds, and private clouds. Any or all of these may be serviced by third party entities. However, in certain examples, private clouds or hybrid clouds may allow for sharing of sequence data and services among authorized users.

A cloud facility 912 includes a plurality of computer systems/nodes 914. The computing resources of the nodes 914 may be pooled to serve multiple consumers, with different physical and virtual resources dynamically assigned and reassigned according to consumer demand. Examples of resources include storage, processing, memory, network bandwidth, and virtual machines. The nodes 914 may communicate with one another to distribute resources, and such communication and management of distribution of resources may be controlled by a cloud management module residing in one or more nodes 914. The nodes 914 may communicate via any suitable arrangement and protocol. Further, the nodes 914 may include servers associated with one or more providers. For example, certain programs or software platforms may be accessed via a set of nodes 914 provided by the owner of the programs while other nodes 914 are provided by data storage companies. Certain nodes 914 may also be overflow nodes that are used during higher load times.

In one example, a cloud management module is responsible for load management and cloud resources. The load management may be implemented through consideration of a variety of factors, including user access level and/or total load in the cloud computing environment (peak times versus average load times). The project type may also be considered. In one example, public health emergencies may be prioritized over other types of projects. Further, a user may manage costs by offering certain runs as lower priority that are held until cloud usage is below a certain threshold.

The cloud facility 912 is configured to communicate with various users (e.g. user computer systems) for generating biological data. Such data may include sequence data generated via a sequencing device 916, which in particular examples may include a sequencing device 918 that includes a module to accept a biological sample and generate sequence data and an associated computer 920 that includes executable instructions for analyzing or communicating the sequence data to the cloud facility 912. It should be understood that, in certain examples, the sequencing device 916 may also be implemented as an all-in-one device. The sequencing device 916 is configured to communicate with the cloud facility 912 via a suitable communications link 924. The communication with the cloud facility 912 may include communication via a local area network (LAN), a general wide area network (WAN), and/or a public network (e.g., the Internet) via the communications link 924. In particular, the communications link 924 sends sequence data 926 and, in certain examples, authentication information 928, to the cloud computing environment 912. The authentication information may confirm that the sequencing device 916 is a client of the cloud facility 912.

As noted, the cloud facility 912 may serve multiple users or clients with associated devices, e.g., devices 916a, 916b, and 916c. Further, the cloud facility 912 may also be accessed by other types of clients, such as secondary users 930 or third party software holders. Accordingly, the cloud facility 912 may provide different types of services depending on the access level of the particular client. A sequencing client may have access to storage and data analysis services, while a secondary user 930 may have access only to shared or public sequences. Third party software holders may negotiate with sequencing clients to determine appropriate access privileges. For example, open source software may be offered for free or on limited license basis, while other types of software may be offered according to various fee or subscription bases.

Further, a primary user (or secondary user) may also interact with the cloud facility 912 through any appropriate access device, such as a mobile device or other computer system that includes components similar to those described with regard to the computer 920. That is, once the sequence data has been communicated to the cloud facility 912, further interaction with and access to the sequence data may not necessarily be coupled to the sequence device 916. Such examples may be beneficial in examples in which the owner of the biological sample and/or sequence data has contracted for sequencing, e.g., to a core laboratory facility. In such examples, the primary user may be the owner while the core laboratory facility associated with the sequencing device 916 is at most a secondary user after the sequence data has been communicated to the cloud facility 912. In certain examples, the sequence data may be accessed through security parameters such as a password-protected client account in the cloud facility 912 or association with a particular institution or IP address. The sequence data may be accessed by downloading one or more files from the cloud facility 912 or by logging into a web-based interface or software program that provides a graphical user display in which the sequence data is depicted as text, images, and/or hyperlinks. In such an example, the sequence data may be provided to the primary or secondary user in the form of data packets transmitted via a communications link or network.

The cloud facility 912 may execute user interaction software (e.g., via a web-based interface or application platform) that provides a graphical user interface for users and that facilitates access to sequence data, a community or group of researchers, data analysis programs, available third party software, and user selections for load balancing and instrument settings. For example, in particular examples, settings for a sequencing run on a sequencing device 916 may be set via the cloud facility 912. Accordingly, the cloud facility 912 and an individual sequencing device 916 may be capable of two-way communication. Such an example may be particularly useful for controlling parameters of a remote sequencing run.

Results of a sequencing run and various analyses can be stored in files taking the form of FASTQ files, binary alignment files (bam), *.bcl, *.vcf, and/or *.csv files, as examples. The output files may be in formats that are compatible with sequence data viewing, modification, annotation, manipulation, alignment, and realignment software. Accordingly, accessible sequence alignment datasets may be in the form of raw data, partially processed or processed data, and/or data files compatible with particular software programs. In this regard, a computer system, such as a computer system of or in communication with a sequencing device, or a cloud facility computer system, as examples, can obtain a bam or other sequencing alignment dataset and process the file by, for instance, reading its data and performing operations to carrying out aspects described herein. The computer system can then output a file having sequencing alignment data, for instance another bam file. Further, the output files may be compatible with other data sharing platforms or third party software.

The present disclosure may be a system, a method, and/or a computer program product, any of which may be configured to perform or facilitate aspects described herein.

In some examples, aspects of the present disclosure may take the form of a computer program product, which may be embodied as computer readable medium(s). A computer readable medium may be a tangible storage device/medium having computer readable program code/instructions stored thereon. Example computer readable medium(s) include, but are not limited to, electronic, magnetic, optical, or semiconductor storage devices or systems, or any combination of the foregoing. Example implementations of a computer readable medium include a hard drive or other mass-storage device, an electrical connection having wires, random access memory (RAM), read-only memory (ROM), erasable-programmable read-only memory such as EPROM or flash memory, an optical fiber, a portable computer disk/diskette, such as a compact disc read-only memory (CD-ROM) or Digital Versatile Disc (DVD), an optical storage device, a magnetic storage device, or any combination of the foregoing. The computer readable medium may be readable by a processor, processing unit, or the like, to obtain data (e.g. instructions) from the medium for execution. In a particular example, a computer program product is or includes one or more computer readable media that includes/stores computer readable program code to provide and facilitate one or more aspects described herein.

As noted, program instruction contained or stored in/on a computer readable medium can be obtained and executed by any of various suitable components such as a processor of a computer system to cause the computer system to behave and function in a particular manner. Such program instructions for carrying out operations to perform, achieve, or facilitate aspects described herein may be written in, or compiled from code written in, any desired programming language. In some examples, such programming language includes object-oriented and/or procedural programming languages such as C, C++, C #, Java, etc.

Program code can include one or more program instructions obtained for execution by one or more processors. Computer program instructions may be provided to one or more processors of, e.g., one or more computer systems, to produce a machine, such that the program instructions, when executed by the one or more processors, perform, achieve, or facilitate aspects of the present disclosure, such as actions or functions described in flowcharts and/or block diagrams described herein. Thus, each block, or combinations of blocks, of the flowchart illustrations and/or block diagrams depicted and described herein can be implemented, in some examples, by computer program instructions.

Although various examples are described above, these are only examples. For example, computing environments of other architectures can be used to incorporate and use one or more examples.

The terminology used herein is for the purpose of describing particular examples only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more examples has been presented for purposes of illustration and description, but is not intended to be exhaustive or limited to in the form disclosed. Many modifications and variations will be apparent to those of ordinary skill in the art. The example was chosen and described in order to best explain various aspects and the practical application, and to enable others of ordinary skill in the art to understand various examples with various modifications as are suited to the particular use contemplated.

The terms "substantially", "approximately", "about", "relatively," or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A computer-implemented method for sequencing a biological sample, the method comprising:
obtaining a plurality of images; and
distributing the plurality of images to a plurality of processing engines for coordinated application processing, the plurality of processing engines to perform image processing, wherein the plurality of images cover an image area in which the biological sample to be sequenced is present, the image area comprising multiple different sub-areas that each correlate to a respective area of a flow cell, wherein the plurality of images comprise images of a sequence of bases, of the biological sample, to be sequenced, wherein the image processing proceeds across multiple cycles of image processing to process a respective set of images, of the plurality of images, of each sub-area of the different sub-areas, and therefore of the respective area, of the flow cell, to which that sub-area correlates, and wherein the distributing the plurality of images comprises, for each sub-area of the different sub-areas:
distributing, at each cycle of the multiple cycles of the image processing, images, of the respective set of images of the sub-area, taken at that cycle to a respective processing engine, of a plurality of processing engines, associated with, and selected for, processing the respective set of images of the sub-area taken at each cycle of the multiple cycles of the image processing.

2. The method of claim 1, wherein each processing engine of the plurality of processing engines comprises a same application package for instantiation to perform, on images received by the respective processing engine, a same set of tasks as other processing engines of the plurality of processing engines perform on images received by the other processing engines.

3. The method of claim 2, further comprising maintaining an image acquisition component to obtain the plurality of images and provide the plurality of images for distribution, wherein the image acquisition component is part of an application collector to perform in an image acquisition and distribution mode different from a mode under which a respective application collector on each of the plurality of processing engines is to perform.

4. The method of claim 3, wherein the image acquisition component acquires the plurality of images from an imaging device and wherein the method further comprises receiving, from the plurality of processing engines during performance of the image processing, scanning position information indicating guidance for an image scanning engine of the imaging device in acquiring at least some images of the plurality of images.

5. The method of claim 1, wherein each sub-area of the different sub-areas of the image area corresponds to a different set of one or more camera frame positions.

6. The method of claim 1, wherein the plurality of images are acquired during a real-time sequence analysis run to perform sequencing of the sequence of bases, and wherein the distributing the plurality of images distributes the plurality of images in real-time during the real-time sequence analysis run.

7. The method of claim 1, further comprising gathering, from each processing engine of the plurality of processing engines, one or more application completion communications indicating that a respective one or more portions of the image processing assigned to that processing engine are complete.

8. The method of claim 7, further comprising:
maintaining an image processing status of each processing engine of the plurality of processing engines using, at least in part, received or to-be-received application completion communications; and
conveying indications of image processing status of each processing engine to a control component requesting such indications.

9. The method of claim 1, wherein each processing engine of the plurality of processing engines is a different physical host computer system or different virtual machine.

10. The method of claim 1, wherein a first processing engine of the plurality of processing engine is associated with, and selected for, processing a first set of images of a first sub-area of the different sub-areas and wherein a second processing engine of the plurality of processing engine is associated with, and selected for, processing a second set of images of a second sub-area of the different sub-areas.

11. The method of claim 10, wherein a same processing engine of the plurality of processing engines is associated with, and selected for, processing multiples sets of images of at least two sub-areas of the different sub-areas.

12. A computer system for sequencing a biological sample, the computer system comprising memory and at least one processor, the computer system to execute program instructions to perform a method comprising:
obtaining a plurality of images; and
distributing the plurality of images to a plurality of processing engines for coordinated application processing, the plurality of processing engines to perform image processing, wherein the plurality of images cover an image area in which the biological sample to be sequenced is present, the image area comprising multiple different sub-areas that each correlate to a respective area of a flow cell, wherein the plurality of images comprise images of a sequence of bases, of the biological sample, to be sequenced, wherein the image processing proceeds across multiple cycles of image processing to process a respective set of images, of the plurality of images, of each sub-area of the different sub-areas, and therefore of the respective area, of the flow cell, to which that sub-area correlates, and wherein the distributing the plurality of images comprises, for each sub-area of the different sub-areas:

distributing, at each cycle of the multiple cycles of the image processing, images, of the respective set of images of the sub-area, taken at that cycle to a respective processing engine, of a plurality of processing engines, associated with, and selected for, processing the respective set of images of the sub-area taken at each cycle of the multiple cycles of the image processing.

13. The computer system of claim 12, wherein each processing engine of the plurality of processing engines comprises a same application package for instantiation to perform, on images received by the respective processing engine, a same set of tasks as other processing engines of the plurality of processing engines perform on images received by the other processing engines.

14. The computer system of claim 13, maintaining an image acquisition component to obtain the plurality of images and provide the plurality of images for distribution, wherein the image acquisition component is part of an application collector to perform in an image acquisition and distribution mode different from a mode under which a respective application collector on each of the plurality of processing engines is to perform.

15. The computer system of claim 14, wherein the image acquisition component acquires the plurality of images from an imaging device and wherein the method further comprises receiving, from the plurality of processing engines during performance of the image processing, scanning position information indicating guidance for an image scanning engine of the imaging device in acquiring at least some images of the plurality of images.

16. The computer system of claim 12, wherein the plurality of images are acquired during a real-time sequence analysis run to perform sequencing of the sequence of bases, and wherein the distributing the plurality of images distributes the plurality of images in real-time during the real-time sequence analysis run.

17. A computer program product for sequencing a biological sample, the computer program product comprising:
a non-transitory computer readable storage medium storing program instructions for execution to perform a method comprising:
obtaining a plurality of images; and
distributing the plurality of images to a plurality of processing engines for coordinated application processing, the plurality of processing engines to perform image processing, wherein the plurality of images cover an image area in which the biological sample to be sequenced is present, the image area comprising multiple different sub-areas that each correlate to a respective area of a flow cell, wherein the plurality of images comprise images of a sequence of bases, of the biological sample, to be sequenced, wherein the image processing proceeds across multiple cycles of image processing to process a respective set of images, of the plurality of images, of each sub-area of the different sub-areas, and therefore of the respective area, of the flow cell, to which that sub-area correlates, and wherein the distributing the plurality of images comprises, for each sub-area of the different sub-areas:
distributing, at each cycle of the multiple cycles of the image processing, images, of the respective set of images of the sub-area taken at that cycle to a respective processing engine, of a plurality of processing engines, associated with, and selected for, processing the respective set of images of the sub-area taken at each cycle of the multiple cycles of the image processing.

18. The computer program product of claim 17, wherein each processing engine of the plurality of processing engines comprises a same application package for instantiation to perform, on images received by the respective processing engine, a same set of tasks as other processing engines of the plurality of processing engines perform on images received by the other processing engines.

19. The computer program product of claim 18, wherein the method further comprises maintaining an image acquisition component to obtain the plurality of images and provide the plurality of images for distribution, wherein the image acquisition component is part of an application collector to perform in an image acquisition and distribution mode different from a mode under which a respective application collector on each of the plurality of processing engines is to perform.

20. The computer program product of claim 19, wherein the image acquisition component acquires the plurality of images from an imaging device and wherein the method further comprises receiving, from the plurality of processing engines during performance of the image processing, scanning position information indicating guidance for an image scanning engine of the imaging device in acquiring at least some images of the plurality of images.

* * * * *